United States Patent [19]

Aebischer et al.

[11] Patent Number: 5,554,148
[45] Date of Patent: Sep. 10, 1996

[54] RENEWABLE NEURAL IMPLANT DEVICE AND METHOD

[75] Inventors: Patrick Aebischer, Barrington, R.I.; Paul C. DiCesare, Norwalk, Conn.; Moses Goddard, Tiverton, R.I.; Paul J. Mulhauser, New York, N.Y.

[73] Assignee: Brown University Research Foundation, Providence, R.I.

[21] Appl. No.: 453,571

[22] Filed: May 26, 1995

Related U.S. Application Data

[63] Continuation of Ser. No. 226,389, Apr. 12, 1994, abandoned, which is a continuation of Ser. No. 722,950, Jun. 28, 1991, abandoned, which is a continuation-in-part of Ser. No. 369,296, Jun. 21, 1989, abandoned, and Ser. No. 613,109, Nov. 14, 1990, Pat. No. 5,106,627, which is a division of Ser. No. 369,296, which is a continuation-in-part of Ser. No. 121,626, Nov. 17, 1987, Pat. No. 4,892,538.

[51] Int. Cl.$^6$ .................................................. A61K 9/22
[52] U.S. Cl. ......................... 604/890.1; 604/43; 604/93; 604/265
[58] Field of Search .................. 604/27, 29, 93, 604/264, 890.1, 891.1, 264, 265, 174, 175, 93, 43, 282; 128/632, 658–659; 424/424–422

[56] References Cited

U.S. PATENT DOCUMENTS

| | | | |
|---|---|---|---|
| 3,093,831 | 6/1963 | Jordan et al. | 3/1 |
| 3,640,269 | 2/1972 | Delgado | 604/93 |
| 3,911,911 | 10/1975 | Scommegna | 424/432 |
| 4,241,187 | 12/1980 | White | 435/284 |
| 4,309,776 | 1/1982 | Berguer | 424/424 |
| 4,352,883 | 11/1982 | Lim | 11/10 |
| 4,378,016 | 3/1983 | Loeb | 128/260 |
| 4,391,909 | 7/1982 | Lim | 11/10 |
| 4,402,694 | 9/1983 | Ash et al. | 604/891 |
| 4,451,253 | 5/1984 | Harmen | 604/60 |
| 4,479,796 | 10/1984 | Kallock | 604/93 |
| 4,578,057 | 3/1986 | Sussman | 604/167 |
| 4,686,098 | 8/1987 | Kopchick et al. | 424/424 |
| 4,892,538 | 1/1990 | Aebischer et al. | 604/891 |
| 4,902,285 | 2/1990 | Walthall et al. | 623/11 |
| 4,941,874 | 7/1990 | Sandow et al. | 604/60 |
| 4,973,304 | 11/1990 | Graham et al. | 424/424 |
| 5,106,365 | 4/1992 | Hernadez | 128/760 |
| 5,106,627 | 4/1992 | Aebischer et al. | 424/423 |
| 5,191,900 | 3/1993 | Mishra | 604/96 |

FOREIGN PATENT DOCUMENTS

| | | |
|---|---|---|
| 0147939 | 7/1985 | European Pat. Off. . |
| 0304700 | 8/1988 | European Pat. Off. . |
| 2564734 | 11/1985 | France . |
| 2130916 | 6/1984 | United Kingdom . |
| WO84/00304 | 2/1984 | WIPO . |
| WO87/03802 | 7/1987 | WIPO . |
| WO88/10103 | 12/1988 | WIPO . |
| WO8904655 | 6/1989 | WIPO . |
| WO91/00119 | 1/1991 | WIPO . |

OTHER PUBLICATIONS

Tresco et al. (1992) Asaio Journal 38:17–23.
Aebischer et al. (1991) Science 242:133
Winn et al. (1991) Experimental Neurology 113:322–329.
Aebischer et al. (1991) Brain Research 560:43–49.
Aebischer et al. (1991) J. Biomec. Engineering 113:178–183.
Aebischer et al. (1991) Experimental Neurology 111:269–275.

(List continued on next page.)

Primary Examiner—Randall L. Green
Assistant Examiner—Mark Bockleman
Attorney, Agent, or Firm—James F. Haley, Jr., Esq.; Ivor R. Elrifi, Esq.; Fish & Neave

[57] ABSTRACT

Refillable immunoisolatory neurological therapy devices for local and controlled delivery of a biologically active factor to the brain of a patient. The devices include a cell chamber adapted for infusion with nsecretory cells and having at least one semipermeable or permselective surface across which biologically active factors secreted by the cells can be delivered to the brain. The devices also include means for introducing secretory cells into the cell chamber, and means for renewing the cells or cell medium.

29 Claims, 12 Drawing Sheets

OTHER PUBLICATIONS

Aebischer et al. (1991) Biomaterials 12:50–56.
Jaeguer et al. (1991) Brain Research 551:163–170.
Hoffman et al. (1990) Experimental Neurology 110:39–44.
Winn et al. (1989) Experimental Neurology 105:244–250.
Winn et al. (1989) J. Biomed. Mater. Res. 23:31–44.
Aebischer et al. (1988) Brain Reserch 448:364–368.
Jaeger et al. (1990) Progress in Brain Research 82:41–46.
Aebischer et al. "Long–Term Cross–Species Brain Transplanting of a Polymer Encapsulated Dopamine–Secreting Cell Line" *Experimental Neurology* 111, 269–275 (1991).
Bjorklund et al. "Cross–species neural grafting in a rat model of Parkinson's disease" *Nature vol.* 298 12 Aug. 1982, pp. 652–654.
Brundin et al. "Cyclosporin A increases survival of cross–species intrastriatal grafts of embryonic dopamine--containing neurons" *Experimental Brain Research* (1985) 60:204–208.
Calne et al. "L–Dopa in Idiopathic Parkinsonism" *The Lancet*, Nov. 8, 1969, pp. 973–976.
Calne et al. "Bromocriptine in Parkinsonism" *British Medical Journal*, 23 Nov. 1974, pp. 442–444.
M. A. Dichter "The Epilepsies and Convulsive Disorders" *Principals of Internal Medicine* (1983), pp. 2125–2127.
Freed et al. "Transplanted adrenal chromaffin cells in rat brain reduce lesion–induced rotational behavior" *Nature* (1981) 292:351–352.
Hefti et al. "Implantation of PC12 Cells into the Corpus Striatum of Rats with Lesions of the Dopaminergic Nigrostriatal Neurons" *Brain Research*, 348 (1985) 283–288.
Perlow et al. "Brain Grafts Reduce Motor Abnormalities Produced by Destruction of Nigrostriatal Dopamine System" *Science* (1979) 204: 643–647.
Stenass and Stenass, "Hisopathological Evaluation of Materials Implanted in the Cerebral Cortex" *Acta Neuropath (Berl)* (1978) 41:145–155.
Sun et al. "The Use, in Diabetic Rats and Monkeys, of Artificial Capillary Units Containing Cultural Islets of Langerhans (Artificial Endocrine Pancreas)" *Diabetes* (1977) 26:1136–1139.

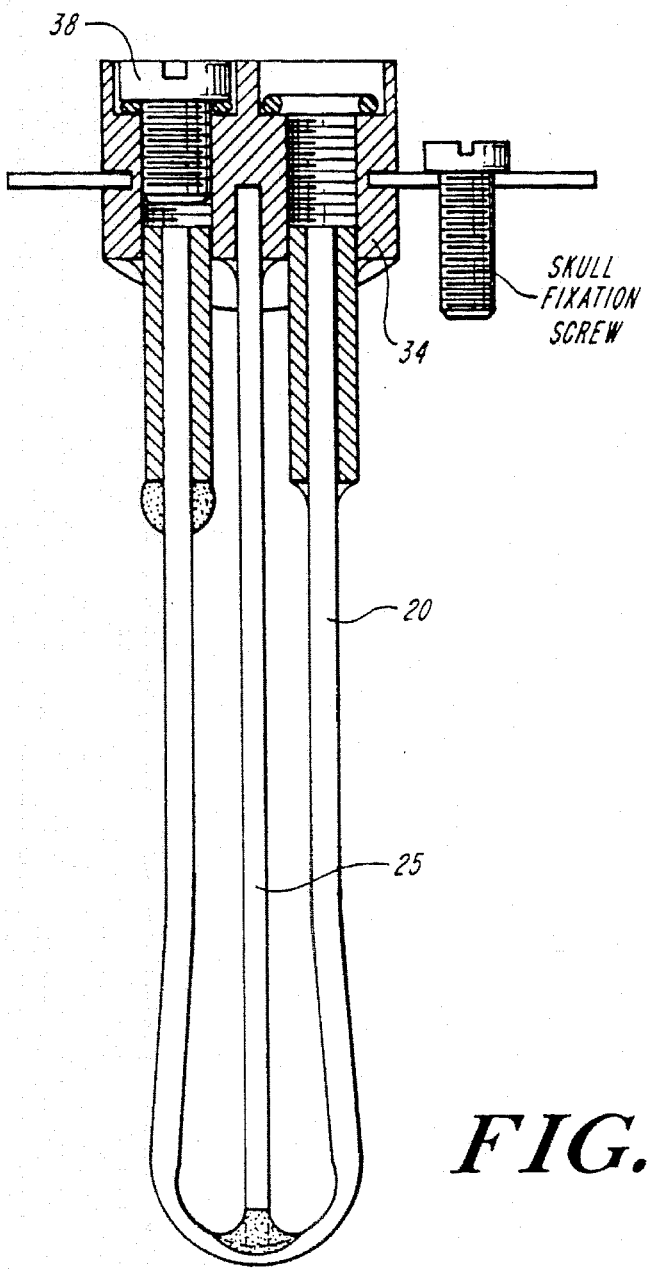
*FIG. 2A*
*FIG.4C*
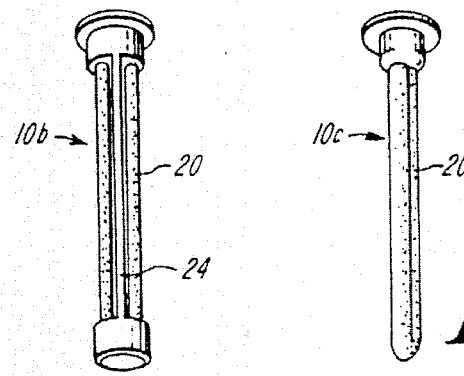
*FIG.2B*
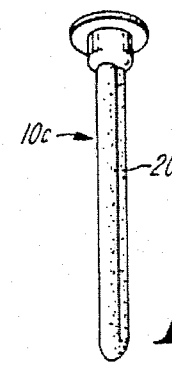
*FIG.2C*
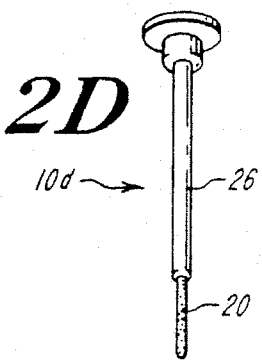
*FIG.2D*

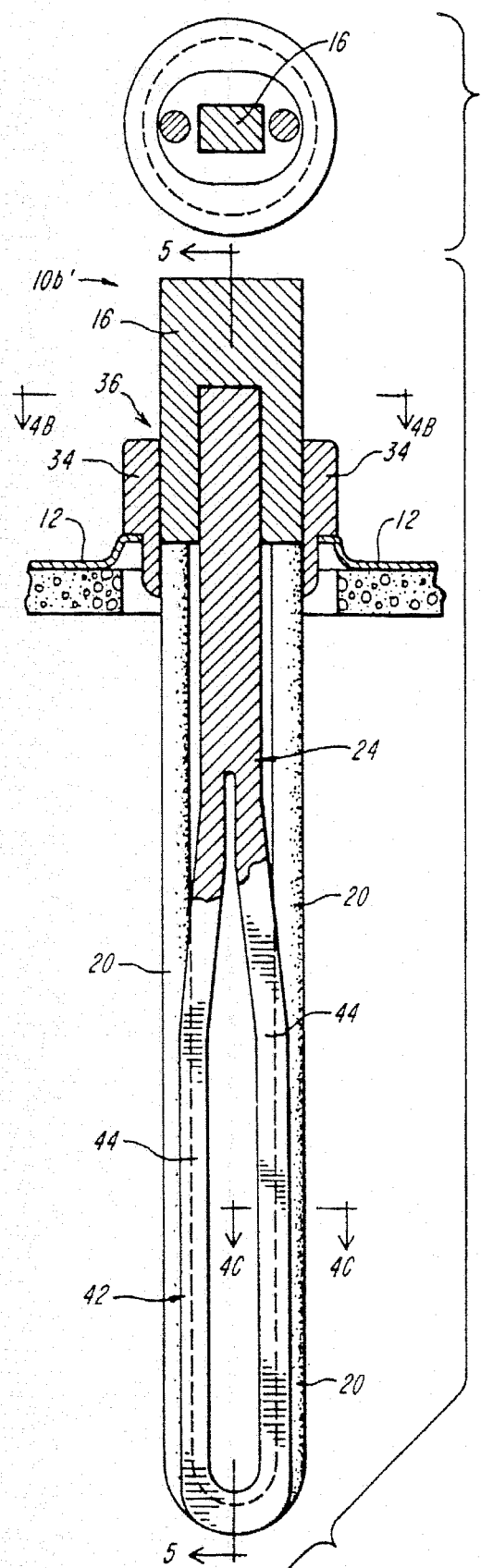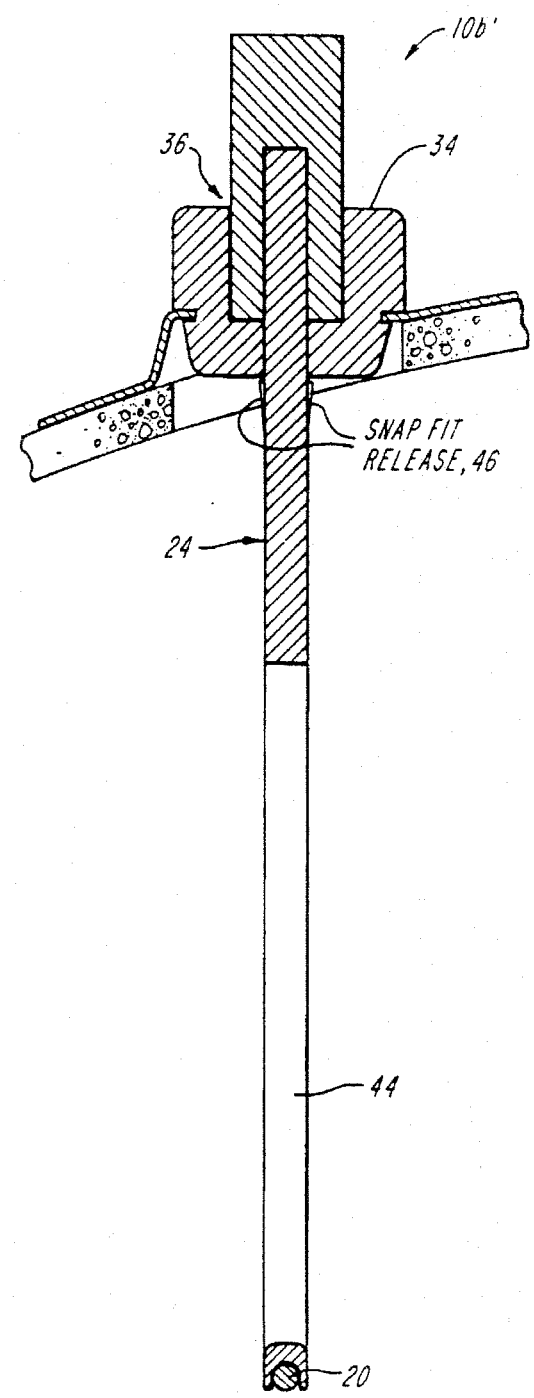
FIG. 4B
FIG. 4A
FIG. 5

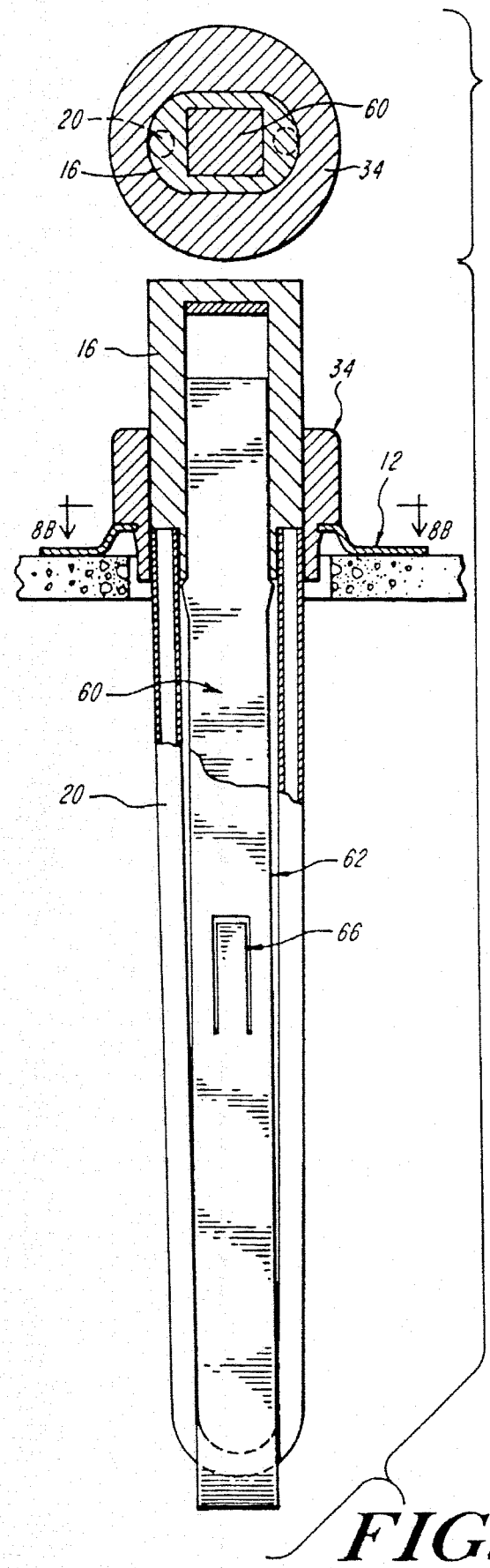
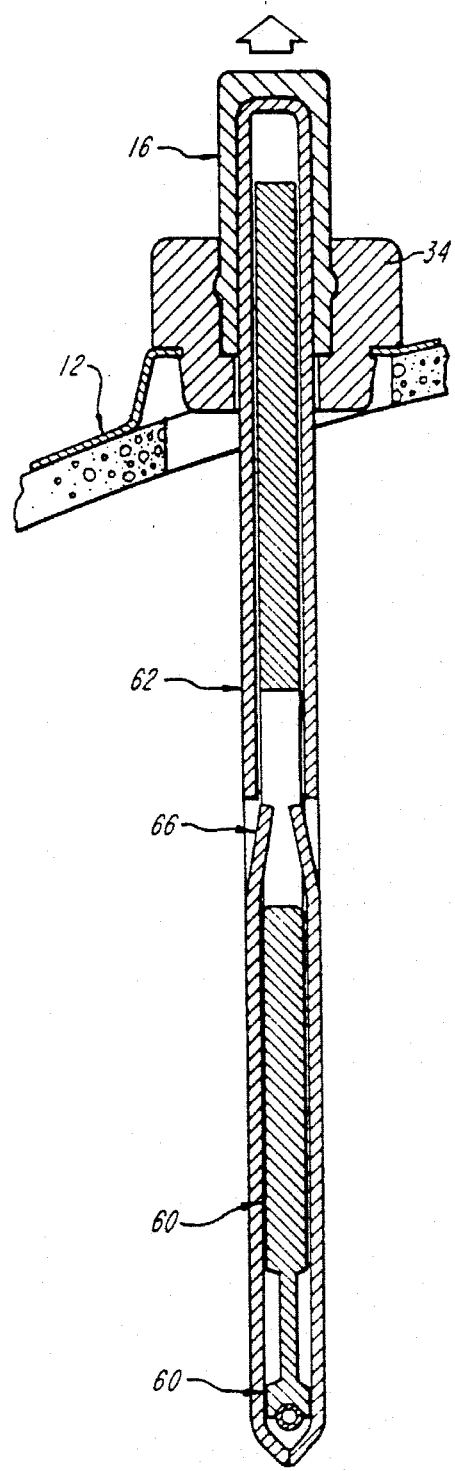
FIG. 8B
FIG. 8A   FIG. 9

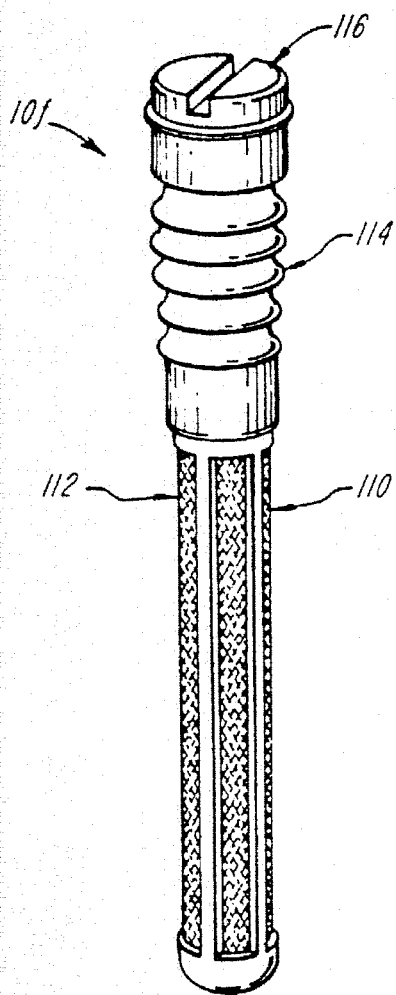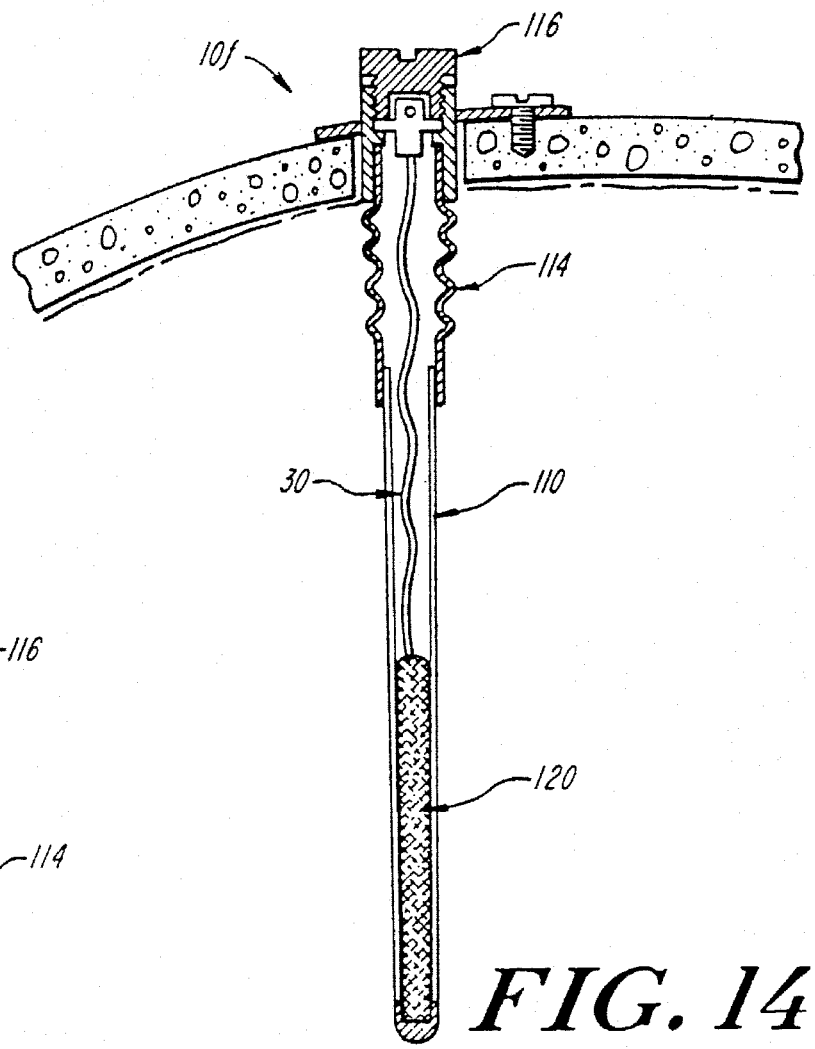
FIG. 13
FIG. 14

RENEWABLE NEURAL IMPLANT DEVICE AND METHOD

CROSS-REFERENCE TO RELATED APPLICATION

This application is a continuation of No. 08/226,389, filed Apr. 12, 1994, now abandoned which is a continuation of Ser. No. 07/722,950, filed Jun. 28, 1991, now abandoned which is a continuation-in-part of U.S. patent application Ser. No. 369,296 filed Jun. 21, 1989, entitled "Neurological Therapy Devices", now abandoned which is a continuation-in-part of U.S. patent application Ser. No. 121,626, filed Nov. 17, 1987, entitled "In Vivo Delivery of Neurotransmitters by Implanted, Encapsulated Cells", now U.S. Pat. No. 4,892,538, said 07/722,950 also being a continuation-in-part of U.S. patent application Ser. No. 07/613,109, filed Nov. 14, 1990, and entitled "Neurological Therapy Devices", now U.S. Pat. No. 5,106,627, which is a division of U.S. patent application Ser. No. 369,296 (now abandoned).

BACKGROUND OF THE INVENTION

The technical field of this invention is the treatment of neurological disorders and, in particular, the treatment of diseases and disorders which may be remedied by treatment with secretory substances, such as neurotransmitters, neuromodulators, hormones, trophic factors, or growth factors. All these substances are characterized by the fact they are secreted by "source" cells and produce a specific change in the source cell itself or in a "target" cell (i.e., they are biologically active).

Deficits in secretory substances have been implicated in various neurological diseases. Lack of neurotransmitter-mediated synaptic contact causes neuropathological symptoms, and can also lead to the ultimate destruction of the neurons involved.

For example, paralysis agitans, more commonly known as Parkinson's disease, is characterized by a lack of the neurotransmitter, dopamine, within the striatum of the brain, secondary to the destruction of the dopamine secreting cells of the substantia nigra. Affected subjects demonstrate a stooped posture, stiffness and slowness of movement, and rhythmic tremor of limbs, with dementia being often encountered in very advanced stages of the disease.

The direct administration of purified or synthetic dopamine, its precursors, analogs and inhibitors have been studied for therapeutic value in the treatment of Parkinson's disease. These studies have revealed various problems with delivery, stability, dosage, and cytotoxicity of the applied compounds. To date, none of these approaches has demonstrated more than marginal therapeutic value. Brain derived growth factor also may have potential value in the treatment of Parkinson's disease since it has been demonstrated to maintain the viability of striatal neurons in vitro.

Many other diseases, especially neurological disorders appear to be based in whole, or in part, on the absence or limited availability, to target cells or regions, of a critical biological factor.

In an attempt to provide a continuous supply of drugs or other factors to the brain and other tissues at a controlled rate, miniature osmotic pumps have been used. However, limited solubility and stability of certain drugs, as well as reservoir limitations, have restricted the usefulness of this technology. For example, controlled sustained release of dopamine has been attempted by implanting dopamine encapsulated within bioresorbable microcapsules (McRae-Degueurce et al. (1988) Neurosci. Lett. 92:303–309). However, controlled sustained release of a drug from a bioresorbable polymer relies on bulk surface erosion, for example, due to various hydrolytic events, increasing the likelihood of drug degradation, and rendering predictable release rates difficult.

The implantation of cells capable of constitutively producing and secreting neurologically active factors has also been attempted. Recently, remedial transplantation of neurotransmitter-secreting tissue has been accomplished using the patient's own tissue so as not to elicit an immune response. For example, dopamine-secreting tissue from the adrenal medulla of patients suffering from Parkinson's disease has been implanted in their striatum with some success. However, this procedure is only used in patients less than 60 years of age, as the adrenal gland of older patients may not contain sufficient dopamine-secreting cells. This restriction limits the usefulness of the procedure as a remedy since the disease most often affects older people.

Other transplantation approaches have demonstrated that even though the brain is considered "immuno-privileged", rejection ultimately occurs with both allografts and xenografts. This problem necessitates the co-adminstration of immuno-suppressors, the use of which renders their own set of complications and deleterious side-effects.

A number of researchers have proposed the use of microcapsules, i.e., tiny spheres which encapsulate a microscopic droplet of a cell solution, for both therapeutic implantation purposes and large scale production of biological products. However, there are a number of shortcomings to the microencapsulation approach. For example, the microcapsules can be extremely difficult to handle, including being difficult to retrieve after implantation. The types of encapsulating materials which can be used are constrained by the formation process to polymers which can dissolve in biocompatible solvents. Furthermore, due to the limited diffusional surface area per unit volume of larger size spheres, only a limited amount of tissue can be loaded into a single microcapsule.

An alternative approach has been macroencapsulation, which typically involves loading cells into hollow fibers and then sealing the extremities. In contrast to microcapsules, macrocapsules offer the advantage of easy retrievability, an important feature in therapeutic implants, especially neural implants. However, the construction of macrocapsules in the past has often been tedious and labor intensive. Moreover, due to unreliable closure, conventional methods of macroencapsulation have provided inconsistent results.

Therefore, there exists a need for improved therapies for the treatment of neurological disorders in general, and in particular, a need for therapy devices which can augment or replace the functions of dysfunctional areas of the brain or other organs without causing excessive trauma. More specifically, there exists a need for a method of providing active, neuroactive factor to a localized region of the nervous system of a subject, the correct dosage of which will be constitutively delivered over time.

Accordingly, it is an object of the present invention to provide a method for treating such neurological disorders by delivery of an implantable, renewable neurological therapy device useful for the sustained and controlled delivery of biologically active factors to a subject. More particularly, to provide a method including a renewable device which can deliver biologically active factors to a localized region in the brain of a subject.

It is another object to provide an implantable device that contains and protects biologically active factors therein from in vivo degradation such that it is delivered to the subject in an active form. Yet another object of the present invention is to provide an implantable device which can deliver an amount of biologically active factors responsive to in vivo environmental needs. A further object is to provide an implantable, protective cell culture device which is retrievable, and whose contents are renewable with new and/or additional source of biologically active factors.

SUMMARY OF THE INVENTION

Refillable immunoisolatory therapy devices are disclosed for the local and controlled delivery of a biologically active factor to the brain of a patient. The devices generally include a cell chamber adapted for infusion with biologically active factors, or cells that secrete such factors. The cell chamber includes a semipermeable surface across which the active factors move for delivery to the brain. The devices also include means for introducing such cells or factors to the cell chambers, and a means for renewing the cells or factors.

In one embodiment of the invention, the cell chamber is constructed as a U-shaped tube having ports for filling, flushing, and/or refilling the cell suspension. The ports may be the same or different ports, and can be sealed to prevent introduction of extraneous material into the cell chamber.

In another embodiment, the U-shaped tube may include a support structure, such as a mandrel, for providing structural support to the cell chamber during surgical insertion in the brain. The mandrel may be a solid centerboard mandrel adapted to fit with and support the walls of the U-shaped tube. Alternatively, the mandrel may be a selectively collapsible mandrel that can be removed once the cell chamber is positioned in the brain. The collapsible mandrel may include one or more flanges or tabs which function to secure the mandrel within the U-shape of the cell chamber during insertion.

In another embodiment of the mandrel, a solid centerboard mandrel is initially positioned within the U-shape of the cell chamber, and a substantially rigid shield element is positioned over the mandrel and cell chamber. The entire assembly is then positioned within the brain, and both the mandrel and the shield may be removed. The shield may include tab elements which interfit with an aperture in the solid mandrel to enable these two elements to be removed from the brain substantially simultaneously, leaving the cell chamber in position.

In yet another embodiment of the inventive device, the device may be a coaxial double lumen tube assembly. In that embodiment, the cell chamber is coextruded with a polymer casting solution to form an encapsulated cell chamber. The cell chamber may then be a concentric lumen chamber having ports connected to an inner and an outer lumen for filling, flushing, and/or refilling.

The biologically active factor-secreting cell may include any cell which is known, or has been engineered to produce neuropeptides, trophic factors, or neurotransmitters, or agonists, precursors, active analogs, or active fragments thereof. For example, chromaffin cells of the adrenal medulla, embryonic ventral mesencephalic tissue, and various neuroblastic cell lines such as PC12 function to supply dopamine, and therefore, are preferred for incorporation into the device. In some aspects of the invention, the cell is allospecific (i.e., cells from another of the same species as the subject in which it is to be implanted) or xenospecific (i.e., cells from another of a different species).

The encapsulated cells, or cells contained in the cell chamber of the invention, include neurosecretory cells that secrete biologically active factors such as gamma aminobutyric acid, serotonin, acetylcholine, norepinephrine, endorphins, enkephalins, dopamine, and precursors, agonists, active analogs, and active fragments thereof. The cells may also secrete a dopamine precursor, such as L-dopa, or a dopamine agonist, such as bromocriptine. Other factors, and cells secreting such factors, may be used in practicing the present invention.

The term "biologically active factors" used herein includes neurotransmitters such as gamma aminobutyric acid, serotonin, acetylcholine, epinephrine, norepinephrine, glutamic acid. The term also includes fibroblast growth factors and dopamine. The term further includes precursors, agonists, active analogs, and active fragments of these neurotransmitters (e.g. dopamine precursor L-dopa and dopamine agonist bromocriptine). Cells that secrete peptide factors such as peptide neurotransmitters, growth factors, trophic factors and/or hormones may also be useful. These include: insulin, Factor VIII, trophic factors such as erythropoeitin and growth hormones, biological response modifiers such as lymphokines and cytokines, enzymes, and antibodies from antibody-secreting cells, neuropeptides such as enkephalins, dynorphins, Substance P, and endorphins, as well as factors such as nerve growth factor (NGF), brain-derived neutrophic factor (BDNF), neurotrophin-3 (NT-3), an array of fibroblast growth factors, and an array neurotrophic factor.

The cell chamber may also include a hydrophobic matrix, such as an ethylene vinyl acetate copolymer, or a hydrophilic matrix such as a hydrogel. The cell chambers may be post-production coated or treated with an impermeable outer coating, such as a polyurethane, ethylene vinyl acetate, silicon, or alginate covering part of the cell chamber.

The invention will next be described in connection with certain illustrated embodiments. However, it should be clear that various modifications, additions, and subtractions can be made without departing from the spirit or scope of the invention. For example, the present invention should not be read to require, or be limited to, a particular device shape, material, neurotransmitter, growth factor, or cell line described by way of example or illustration.

BRIEF DESCRIPTION OF THE DRAWINGS

The invention itself can be more fully understood from the following description when read together with the accompanying drawings in which:

FIGS. 2A–2D are side elevation views of cell encapsulation vehicles used in practicing the present invention;

FIG. 4A is a cross-sectional side view of a vehicle embodying the collapsible mandrel of the invention; and FIGS. 4B and 4C are top and bottom cross-sectional views of the vehicle of FIG. 4A, respectively;

FIG. 5 is an orthagonal side view in cross-section of the vehicle of FIG. 4A;

FIG. 8A is a cross-sectional side view of another vehicle embodying the present invention; and FIG. 8B is a top cross-sectional view of the vehicle of FIG. 8A;

FIG. 9 is an orthogonal side view in cross-section of the vehicle of FIG. 8A;

FIG. 13 is a perspective view of another embodiment of a vehicle embodying the invention; and FIG. 14 is a longitudinal-section view of the vehicle of FIG. 13.

Like reference characters in the respective figures indicate corresponding parts.

DETAILED DESCRIPTION

Refillable immunoisolatory neurological therapy devices are disclosed for the constitutive and controlled delivery of biologically active factors to a target treatment site of a patient suffering from a neurological deficiency or dysfunction.

Generally, the inventive device includes a cell chamber for infusion of cells which secrete biologically active factors. The chamber has at least one semipermeable surface across which biologically active factors secreted by the cells can be delivered to the surrounding tissue, such as the brain. The device also includes means for introducing cells to the chamber, and means for renewing the cells contained in the chamber.

Figure 1:
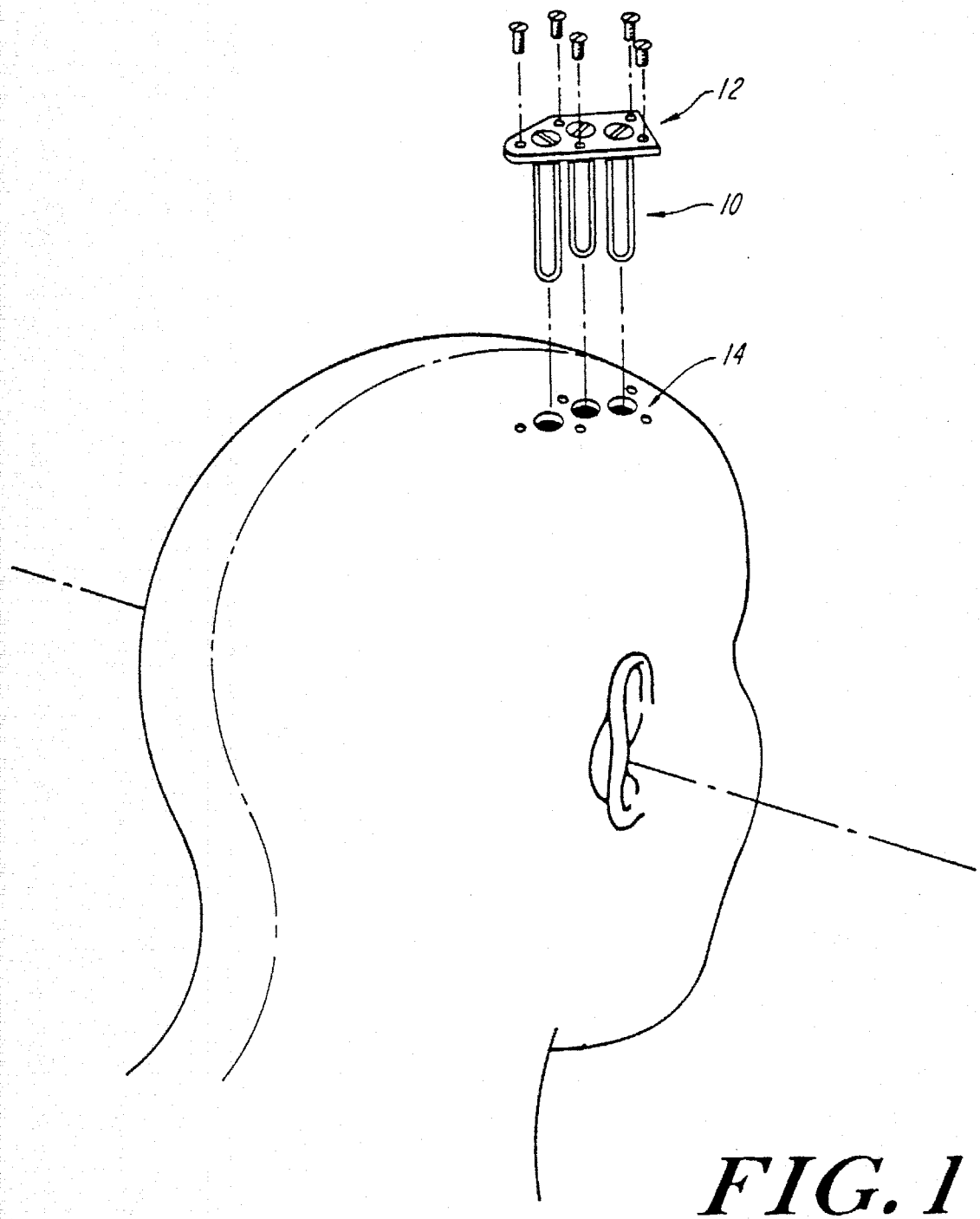
FIG. 1 is a graphic representation of a single plate mount embodying multiples of the system of the present invention.

FIG. 1 illustrates several devices 10 attached to a plate mount 12 positioned above the insertion sites 14 of a patient's skull just prior to delivery to a treatment site. In one form of the invention, and as shown in FIG. 1, the devices 10 may be generally U-shaped. However, as best shown in FIGS. 2A–2E, the devices may have different configurations while performing substantially the same function.

FIG. 2A illustrates a device 10a having a cell chamber 20 that is U-shaped to increase the surface area and having a port 22 for refilling the cell chamber 20. FIG. 2B illustrates a U-shaped cell chamber 20 similar to that of FIG. 2A, including a mandrel 24 to protect the cell chamber 20 during insertion. FIG. 2C illustrates a double lumen device 10c that includes an outer lumen cell chamber 20 for carrying the biologically active factors, and a second inner lumen for flushing the cell chamber cells. FIG. 2d illustrates a single tube 10d having an inner cell chamber 20 containing the neuroactive factors, and an outer protective coating 26 which serves to encase at least part of the cell chamber. The rest of the device 10d is permselective to enable transport of the factors out of the inner cell chamber 20. FIG. 2e illustrates a cell chamber encapsulated in a semi-permeable or permselective membrane 28 with an attached tether 30. The membrane 28 permits diffusion of the neuroactive factors from the cell chamber 20 to the treatment site once the device 10e is positioned. The specific embodiments are discussed in further detail below.

Figure 3:
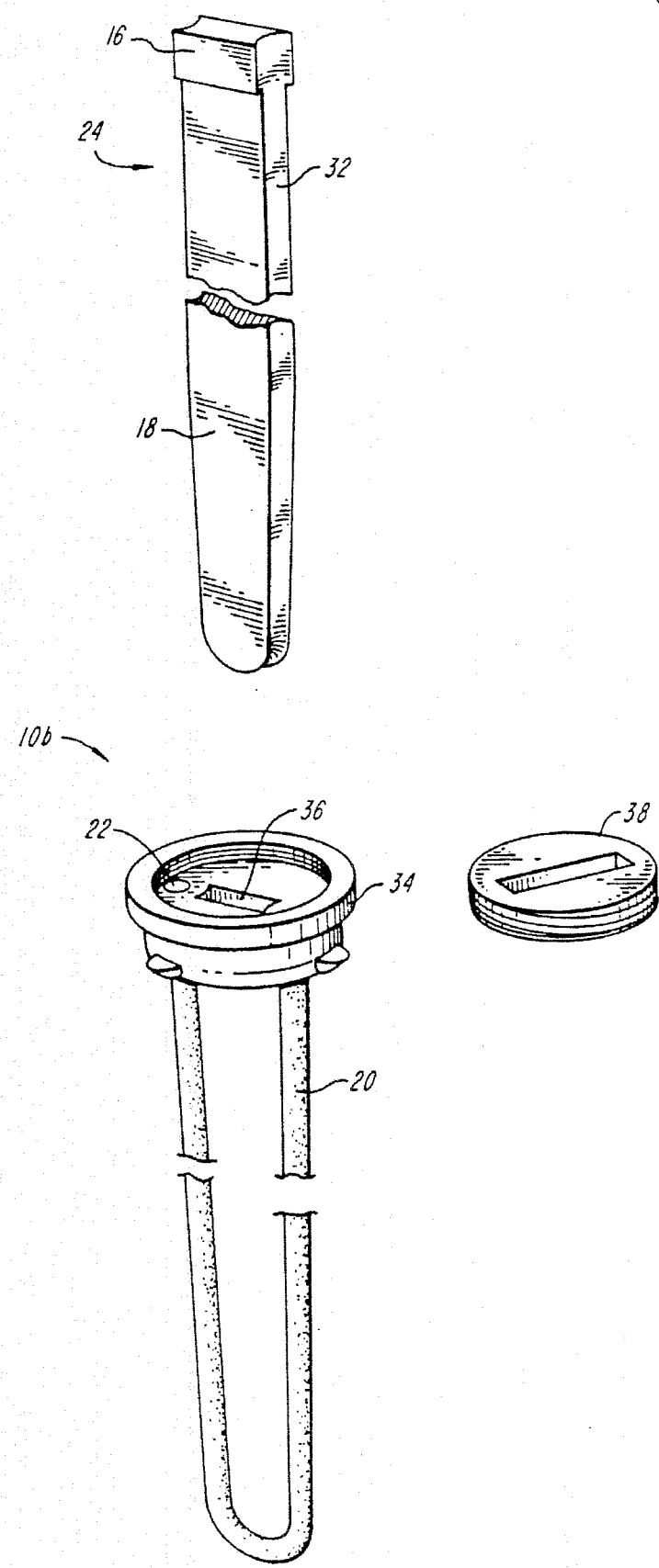
FIG. 3 is a perspective view of a vehicle embodying the centerboard mandrel embodiment of the invention.

Referring to FIG. 3, a standard U-shaped cell chamber 20, of the type shown in FIG. 2A, absent the center supportive strut 25, may be fitted with a centerboard-type mandrel 24 having side slots 32 adapted to receive the cell chamber 20. Since each device 10 of the invention is designed to be mounted to the patient's skull, a cap 34 is attached to the top end portions of the U-shaped cell chamber 20 to secure the shape of the chamber 20. The cap 34 includes the port 22 used for refilling the cell chamber solution.

The mandrel 24 of FIG. 3 is designed to support the U-shaped cell chamber 20 during implantation through the insertion site 14 and to the treatment site in the patient. The mandrel 24 is designed to slidably fit through an insertion port 36 in the cap 34 prior to delivery of the device 10b to the brain. The mandrel 24 includes a solid center plate 18 which is substantially rigid to provide support to the circumferential cell chamber 20. The mandrel 24 further includes a top portion 16 which may act as a stop point during insertion through the insertion port 36.

Because the human brain can move within the cranium, there is strain caused between an implant fixed to the skull and the movable brain tissue. Thus, the mandrel 24 is generally removed after placement of the cell chamber 20 to facilitate flexibility of the chamber 20 once it is positioned. The chamber 20 is generally manufactured from a flexible material to allow the structure to compensate for such movement of the cranium, to which the chamber 20 is attached, relative to the brain, into which the chamber 20 is inserted.

Various polymers and polymer blends can be used to manufacture the cell chamber 20 of the devices of the invention. Polymeric membranes forming the cell chambers may include polyacrylates (including acrylic copolymers), polyvinylidenes, polyvinyl chloride copolymers, polyurethanes, polystyrenes, polyamides, cellulose acetates, cellulose nitrates, polysulfones, polyphosphazeres, polyethylene oxides, polyacrylonitriles, as well as derivatives, copolymers, and mixtures thereof.

The solvents used in conjunction with the above-identified polymers in forming the cell chambers 20 will depend upon the particular polymer chosen for the membrane material. Suitable solvents include a wide variety of organic solvents, such as alcohols and ketones generally, as well as dimethylsulfoxide (DMSO), dimethylacetamide (DMA), and dimethylformimide (DMF). In general, water-miscible organic solvents are preferred.

The polymeric solution, or "dope", can also include various additives, including surfactants to enhance the formation of porous channels, as well as antioxidants to sequester oxides that are formed during the coagulation process. Exemplary surfactants include Triton-X 100 available from Sigma Chemical Corp., and Pluronics P65, P32, and P18. Exemplary anti-oxidants include vitamin C (ascorbic acid) and vitamin E. In addition, anti-inflammatory agents, angiogenic factors, and cell growth factors can also be incorporated into the polymeric membrane to reduce immune response or to stimulate cell culture, respectively. Exemplary anti-inflammatory agents include corticoids such as cortisone and ACTH, dexamethasone, cortisol, interleukin-1 and its receptors and agonists, an antibodies to TGF, to interleukin-1, and to interferon-gamma. Exemplary angiogenic factors include fibroblast growth factor and nerve growth factor. Alternatively, these materials can be added to the devices after manufacture or formation by a post-coating or spraying process. For example, the devices can be immersed in a solution containing an anti-inflammatory agent, an angiogenic factor, or a growth factor.

Post-coating procedures can also be used to provide a protective barrier against immunogens and the like. For example, after formation, the cell chambers can be coated (e.g., by immersion, spraying or applying a flowing fluid during extrusion, if applicable) with a surface protecting material, such as polyehtylene oxide or polyethylene oxide to inhibit protein interactions with the exposed cell chambers. Other protective coatings include silicon, and hydrogels such as alginates.

Various cell types can be encapsulated for use with the present invention. Multi-compartment cell vehicles are particularly useful for the constitutive delivery of neurotransmitters, such as dopamine, which is secreted by cells of the adrenal medulla, embryonic ventral mesencephalic tissue and neuroblastic cell lines. PC12 cells (an immortalized cell line derived from a rat pheocromocytoma) are particularly preferred in some applications because of their ability to secrete large amounts of dopamine and other active factors over long periods of time. Other neurotransmitters include gamma aminobutyric acid (GABA), serotonin, acetylcholine, noradrenaline, peptide neutrotransmitters, and other compounds necessary for normal nerve functions. A number of cell lines are known or can be isolated which secrete these neurotransmitters. Cells can also be employed which synthesize and secrete agonists, analogs, derivatives or fragments of neurotransmitters which are active, including, for example, cells which secrete bromocriptine, a dopamine agonist, and cells which secrete L-dopa, a dopamine precursor.

In other embodiments of the invention, the encapsulated cells can be chosen for their secretion of hormones, cytokines, growth factors, trophic factors, anglogenesis factors, antibodies, blood coagulation factors, lymphokines, enzymes, and other therapeutic agents. Other biologically active factors may include neurotransmitters, peptides, and trophic factors. Exemplary biologically active peptides include enkephalins, endorphins, dynorphin, and Substance P. Exemplary factors include nerve growth factor (NGF), platelet-derived growth factor (PDGF), epidermal growth factor (EGF), brain-derived neurotrophic factor (BDNF), neurotrophin-3 (NT-3), an array of fibroblast growth factors, and ciliary neurotrophic factor.

The aqueous cell suspensions in the cell chambers 20 can further include various additives to protect the cells during the extrusion process or to stimulate their growth subsequently. Such additives may include, for example, a nutrient medium or growth factors which are incorporated into the aqueous suspension, as well as an anchorage substrate material to enhance cell attachment. The anchorage substrate material can be a proteinaceous material, such as collagen, laminin, or polyamino acids. Alternatively, the cell suspension or the polymeric solution (or both) can include a foaming agent or a blowing agent which can distort the inner surface of the polymeric coating to increase the anchorage surface area of the tubular interior.

In the U-shaped cell chamber 20 embodiment of the inventive devices, additional flexibility and strength can be applied to the portion of the cell chamber 20 of the device which extends from the surface of the brain to the filling ports 22 by dipping that portion in a potting solution such as polyurethane.

The inventive device 10 includes a plug 38 which is placed over the cap 34, or fits integral with the cap 34 to cover the filling ports 22 and insertion port 36. The plug 38 may be manufactured from silicone, or any material capable of being formed into the desired configuration. The principle function of such a plug 38 is to keep contaminants out of the ports 22, 36 when the device 10 is in position within a patient.

An alternative embodiment of a mandrel 24 used in supporting the cell chamber 20 in a device of the present invention is shown in FIGS. 4A–4C and 5 which present side and end views of device 10b', respectively. In that illustrated embodiment, the mandrel 24 is collapsible to accommodate for insertion of the mandrel 24 in the U-shaped portion of the device 10b'. As illustrated, the cap 34 is adapted to fit with the plate mount 12. The mandrel 24 includes a top portion 16 to stop the mandrel while it is inserted through the insertion port 36.

The illustrated mandrel 24 of FIGS. 4A–4C further includes a collapsible center portion 42 having side portions 44 which move toward each other during movement through the port 36, and which expand away from each other once they are within the U-shaped portion of the cell chamber 20.

As best shown in FIG. 5, the mandrel 24 may further include flanges 46 that extend from the side portions 44. The flanges 46 are designed to prevent the mandrel 24 from lifting out from between the U-shaped cell chamber 20 during insertion of the device 10b' into the patient's brain. This is achieved by positioning the flanges 46 near the base of the cap 34 so that once the flanges 46 pass entirely through the insertion port 36 and below the cap 34, they form a wedge beneath the cap 34. The entire mandrel 24 may be removed by lifting the top portion 16 along with the mandrel 24 once the cell chamber 20 is in the desired position.

Figure 6:
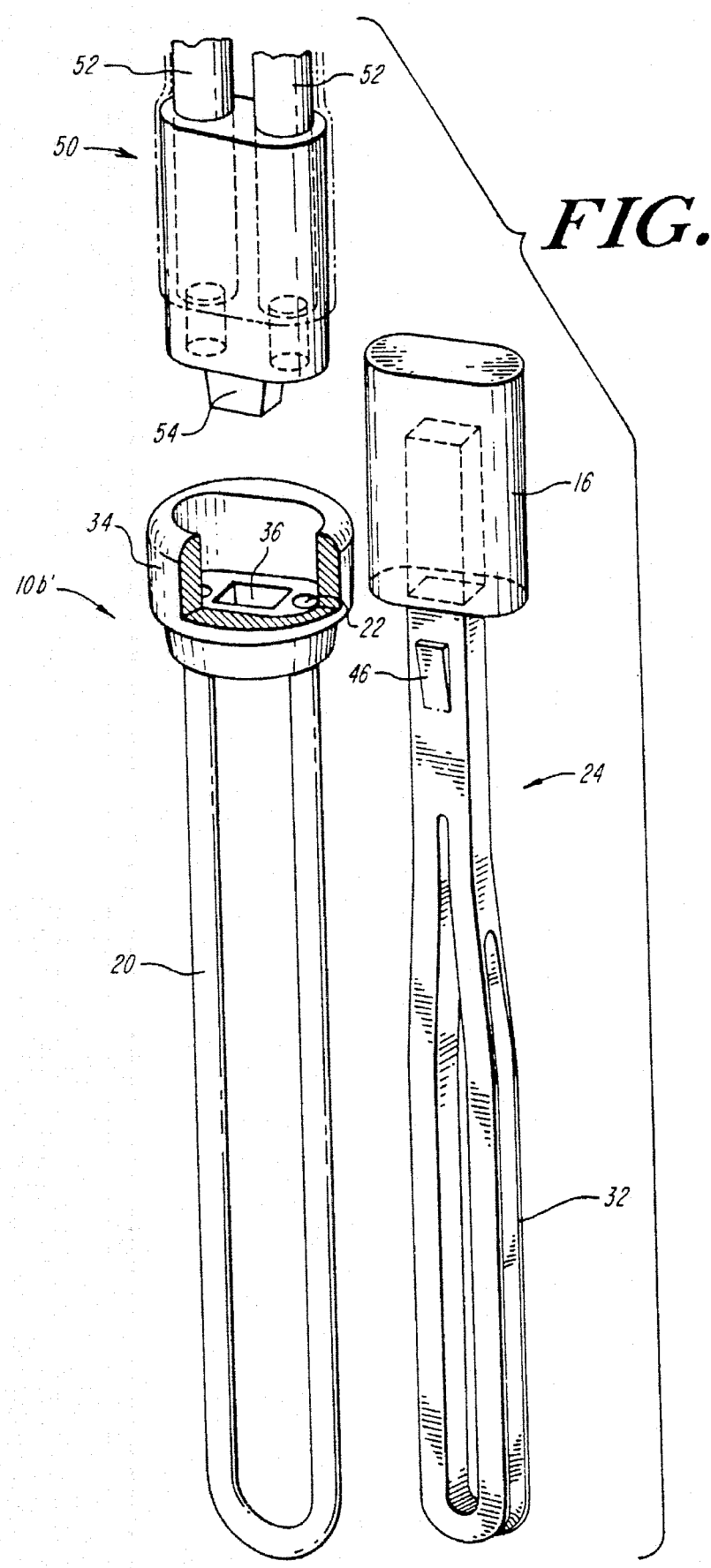
FIG. 6 is a perspective view of a vehicle embodying the present invention.

In using the devices 10 of the present invention, it is desirable to refill or replace the contents of the cell chamber 20. As shown in FIG. 6, this can be achieved by means of a tube sleeve 50. Following removal of the mandrel 24, the sleeve 50 may be inserted into the cap 34 of the device 10b'. The sleeve 50 may include one or more fill tubes 52, each fill tube 52 positioned to align with the fill ports 22 of the device 10b'. The sleeve may further include a flange 54 adapted to interfit with the insertion port 36, which is also used to insert the mandrel 24.

The sleeve 50 may be manufactured from any suitable, maleable material which may be formed into the desired shape. Since the sleeve 50 does not come in direct contact with the patient, there is no specific requirement that it be biocompatible although the sleeve 50 would typically be sterilized before use. Further, since it is a conduit for the tubes 52 carrying biological material, there is no special requirement for it to be compatible with the transported biological material, e.g., biologically active factors.

Figure 7:
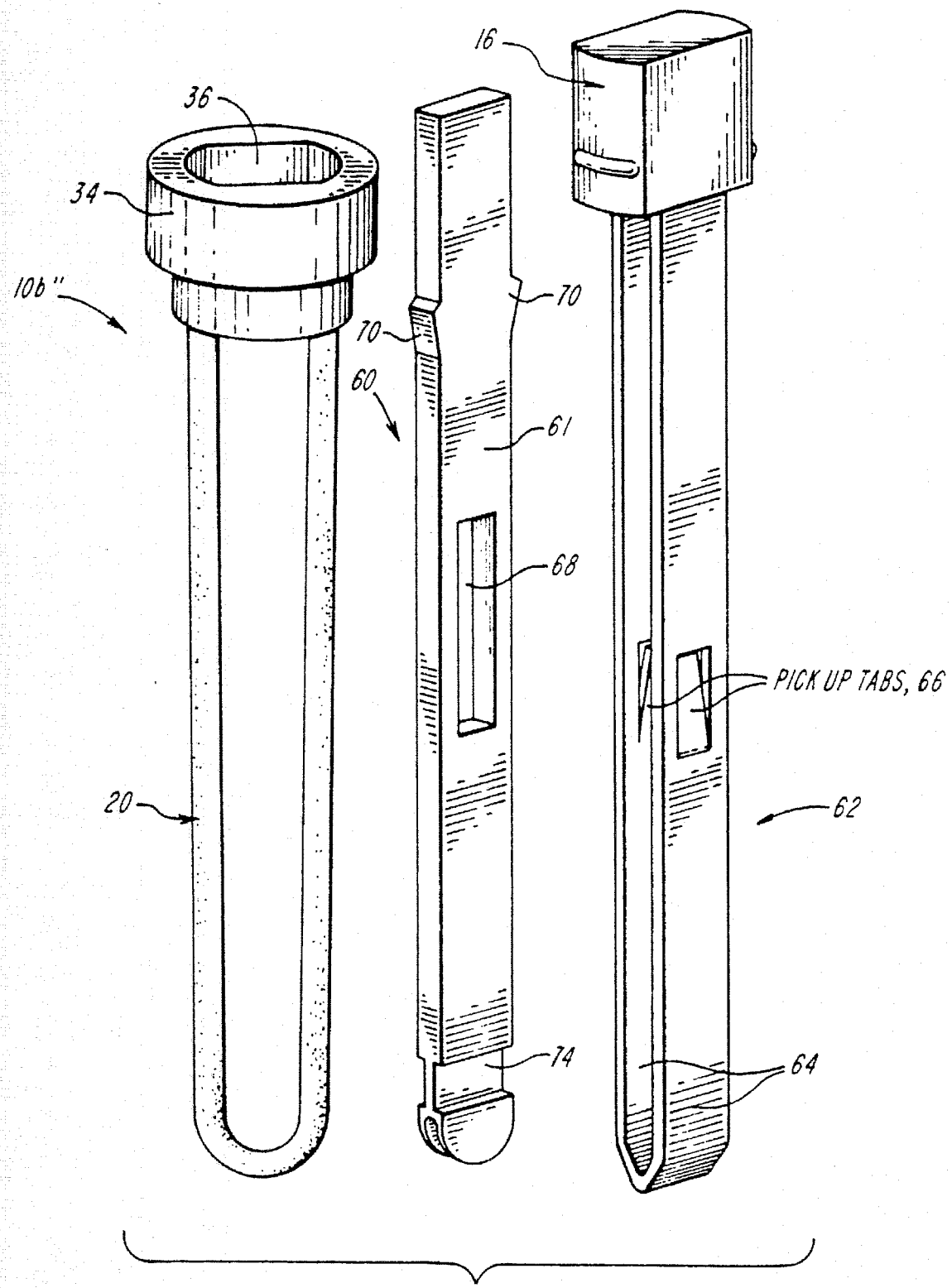
FIG. 7 is a series of perspective views of a vehicle embodying the present invention, which also integrates protective shields about the tip of the implant during surgical placement, which shields are retractable prior to centerboard removal.

An alternative embodiment of the inventive device is shown in FIG. 7. In that illustrated device 10b", the mandrel 24 includes two separate portions: a center mandrel 60, similar to the centerboard mandrel of FIG. 3; and, a shield 62. The center mandrel 60 is held in place within the shield 62 by tabs 66 on one or both legs 64. When the center mandrel 60 is placed between legs 64, the tabs 66 snap into the tab aperture 68 on the center mandrel. In the illustrated embodiment, the center mandrel 60 further includes a ridge 58 on its bottom-most portion adapted to receive the bottom radius of the cell chamber 20.

In practice, and as shown in FIGS. 8A, 8B and 9, the center mandrel 60 slides through the insertion port 36 until the bottom ridge 58 is fitted within and receives the bottom radius of the cell chamber 20. Flanges 70 on the center mandrel snap under the cap 34. Next, the shield 62 is inserted within the insertion port 36, its legs 64 sliding along the walls 61 of the center mandrel. Thus, the legs 64 of the shield cover the walls 61. The legs 64 are generally slightly longer than the length of the center mandrel walls 61 to enable the shield 62 to extend around the entire cell chamber 20 and mandrel 60. The tip portion 72 of each leg 64 may be adapted to form a closure upon positioning of the shield 62, the legs 64 being slightly outwardly flexible to permit the legs to form a gap when being moved into position over the cell chamber 20, yet close once in position.

Figure 10A:
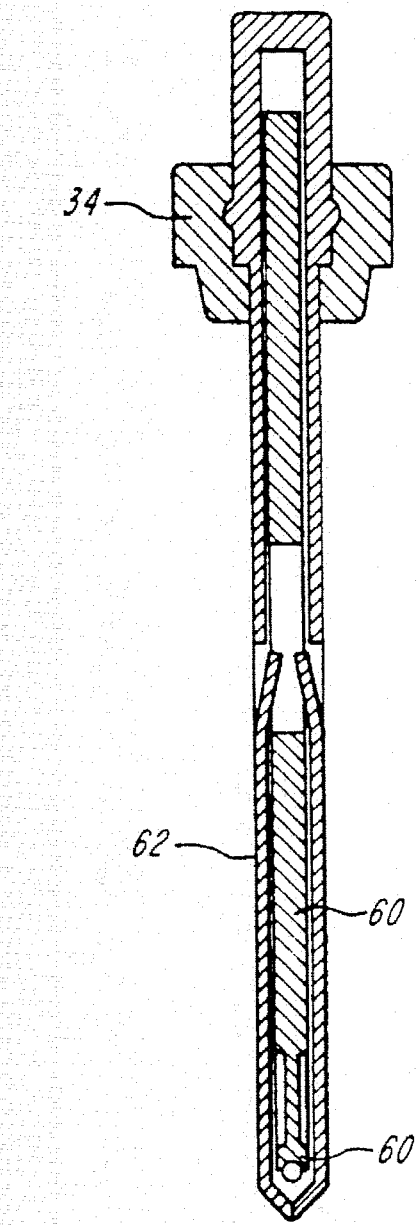
FIGS. 10A–10D are a series of longitudinal-section views of a camming shield embodiment of the invention, the series illustrating operation of the shield.
Figure 10B:
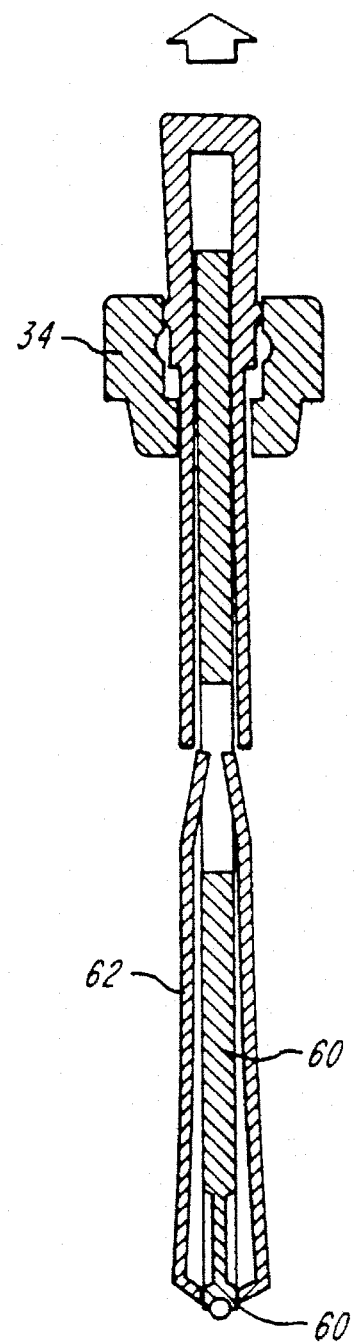
Figure 10C:
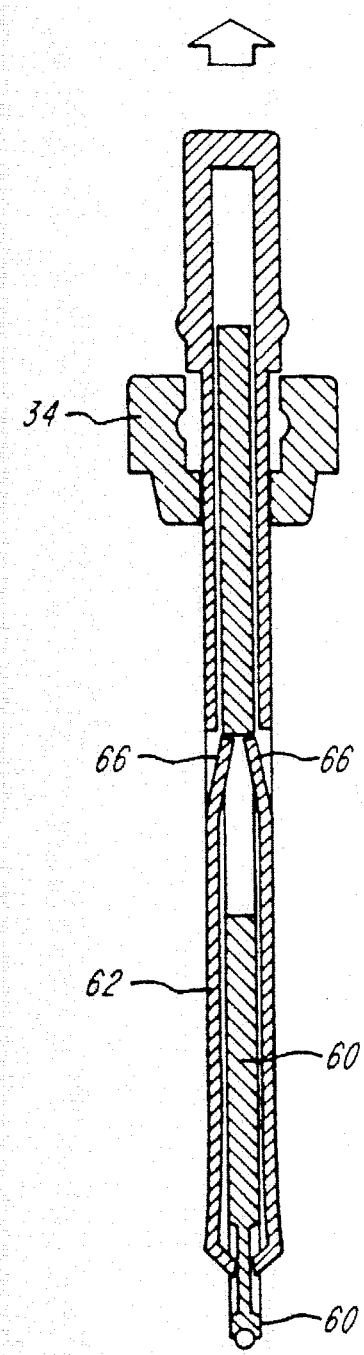
Figure 10D:
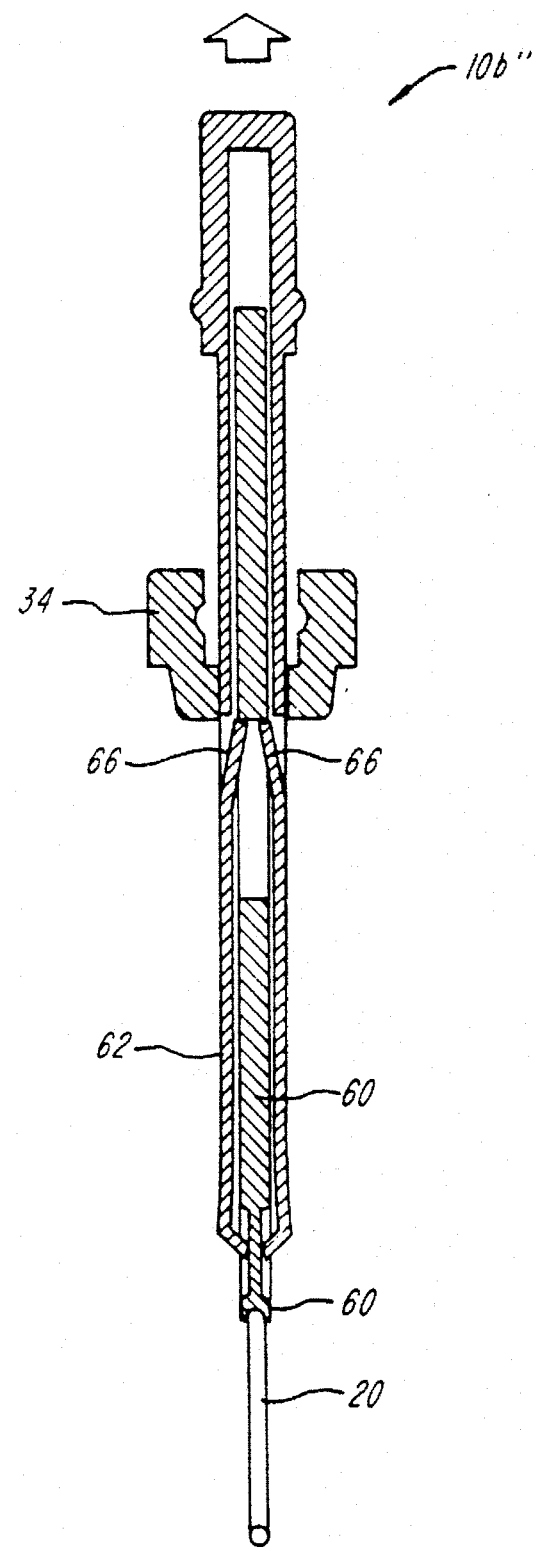

As shown in FIGS. 10A–10D, removal of the center mandrel 60, along with the shield 62 is illustrated. Once the cell chamber (not shown) is positioned, with the inserted center mandrel 60 and overlying shield 62, shown in FIG. 10A, the entire mandrel assembly may be removed. Pulling up on the top portion 16 causes the shield 62 to cam open against the center mandrel by its tabs 66. The legs 64 slightly outwardly flex open to enable them to open around the bottom of the center mandrel wall 70 (shown in FIG. 10B). Next, the shield 62 is retracted, and the tabs 66 engage the center mandrel 60. The tabs 66 inserted in the aperture 68 may be sufficient, or an additional ridge (74 of FIG. 7) on the center mandrel walls may be included to catch the ends of the legs 64 as they move upward out of the insertion port 36. This is shown in FIG. 10C. Finally, as shown in FIG. 10D, the center mandrel 60 and shield 62 are removed. The tabs 66 pull the center mandrel 60 out of the cap 34 through the insertion port 36.

The shield 62 may be made from stainless steel, plastic, or other material capable of being sterilized. Alternatively, the shield and the center mandrel may be manufactured from biocompatible or bioinert material generally commercially available.

Figure 11A:
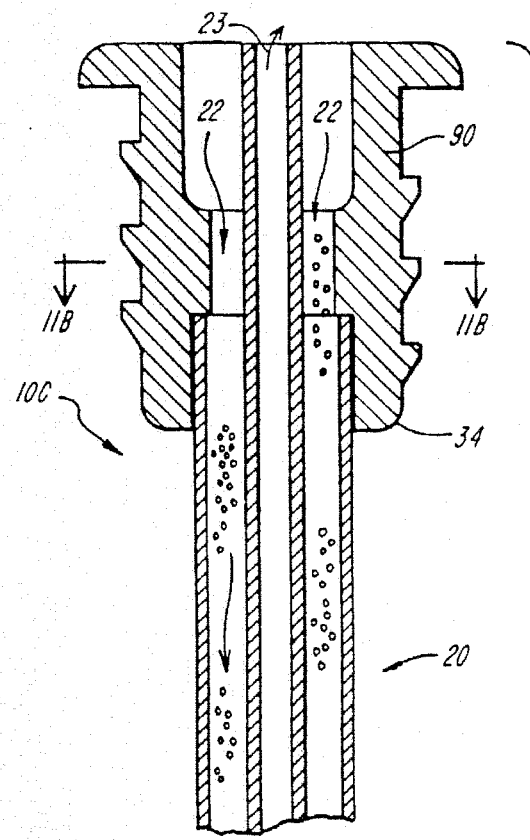
FIG. 11A is a cross-sectional side view of a double lumen vehicle used in practicing the present invention.
Figure 11A:
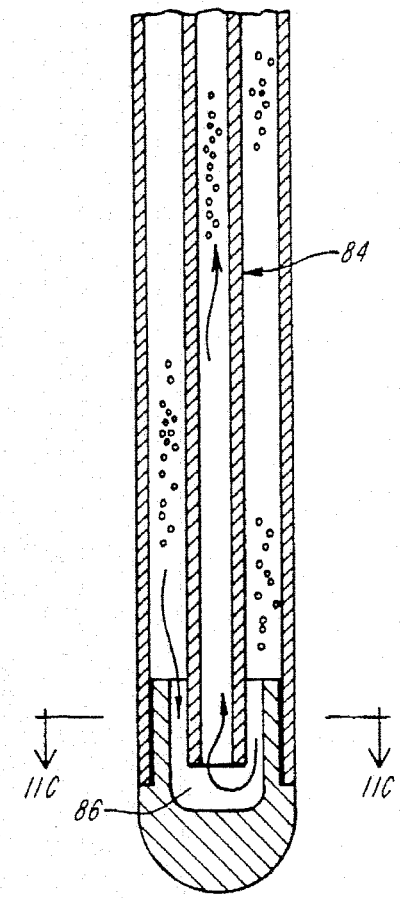
Figure 11B:
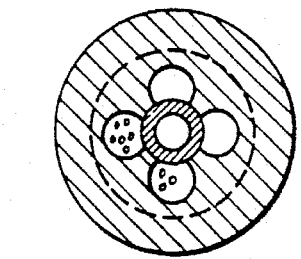
FIGS. 11B and 11C are top and bottom cross-sectional views of the vehicle of FIG. 11A, respectively.
Figure 11C:
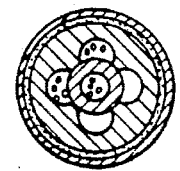

In an alternative embodiment, as shown in FIGS. 11A–11C, the device 10c includes both an inner flushing duct 84 and outer cell chamber tube 84, both of which are biocompatible for cell viability. The outer cell chamber tube 84 may be prepared using hollow fiber extrusion technology, generally known to those skilled in the art. The inner duct 82 can be of any appropriate material manufactured by any appropriate method. Inner tube centering is accomplished through placement of inter-fitting cap 34 and tip 88 portions at either end of the device 10c.

Specifically, referring to FIGS. 11A–11C, the coaxial device 10c includes a cap 34 and cell chamber 20 similar to the other embodiments described in detail above. Along the center axis A—A that runs parallel to the cell chamber walls 82 is a flushing duct 84 for carrying and flushing exhausted or used solution. The bottom portion of the duct is open to a vessel 86 wherein exhausted cell solution is routed up through the flushing duct and out of the device.

The embodiment of FIG. 11 includes a tip portion 88. The tip 88 includes vessel 86, and serves the additional function of assisting in aligning the cell chamber walls 82 with respect to the center flushing duct 84 during construction of the device 10c.

In practice, refilling solution is introduced into the cell chamber walls 82 through the refilling ports 22. The solution flows through the cell chamber 20 and into the vessel 86 at the tip of the device. Old solution, such as depleted cell suspension solution, is forced out of the chamber 20 and up through the inner flushing duct 84, where it is expelled through the expulsion port 23.

Figure 12:
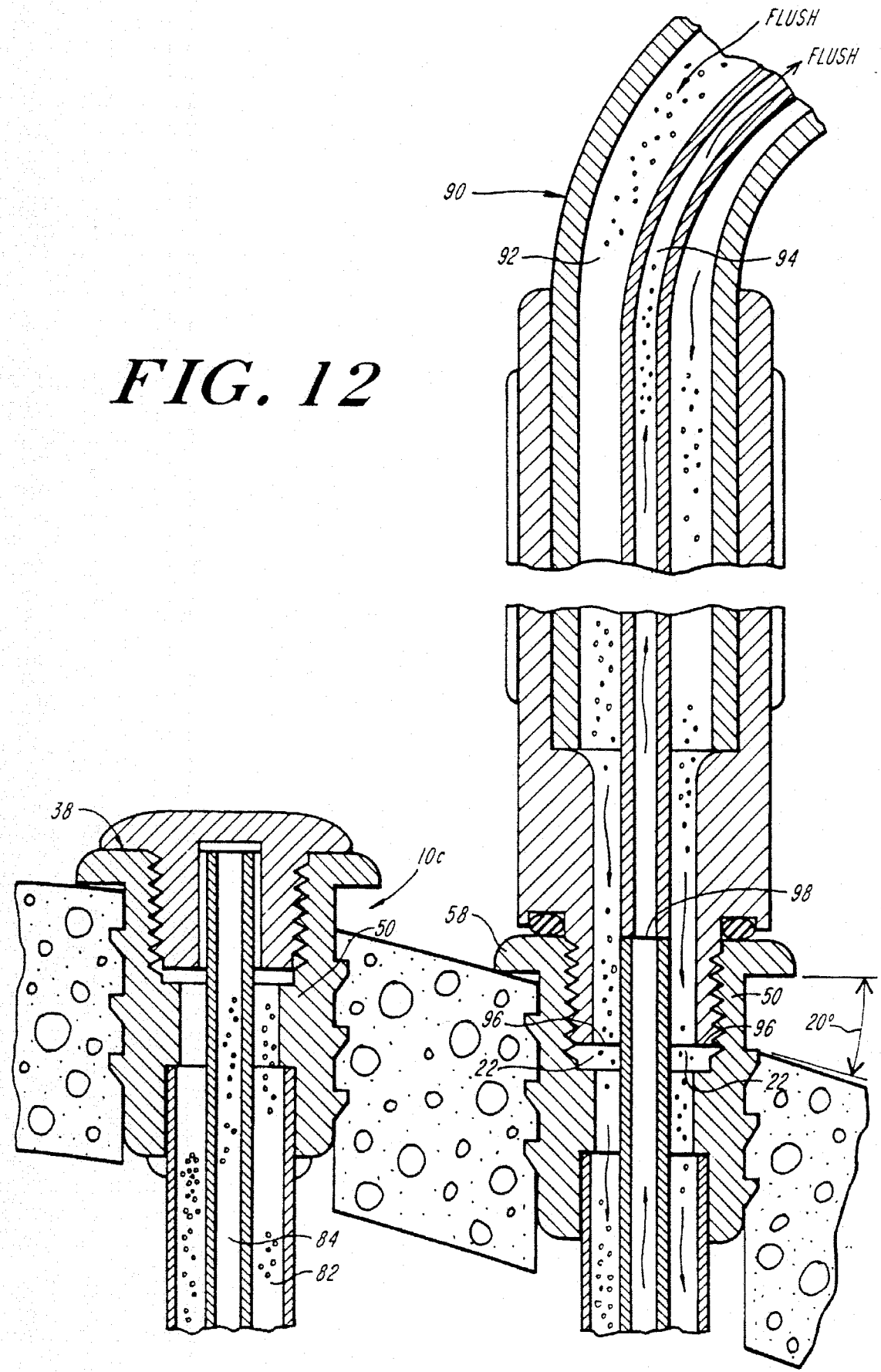
FIG. 12 is a longitudinal-section view of a double lumen embodiment of a vehicle of the present invention, also showing a means for filling/flushing using an applied nozzle.

As best shown in FIG. 12, a fill/flush tube 90 may be adapted to fit with the tube sleeve 50. In operation, when the device 10c is in position within the patient, a plug 38 covers the ports. In the illustrated embodiment, the tube sleeve 50 is threaded on the outer surface to secure it into position either in a plate mount or directly to the skull. The tube sleeve 50 may also have a threaded inner surface for securing a plug 38 having complementary threads, as shown in FIG. 12.

Thus, when it is desirable to flush or refill the cell chamber, the plug 38 is removed and a fill/flush tube 90 is secured into the tube sleeve 50. The end of the fill/flush tube to be inserted within the tube sleeve may be threaded to accommodate the threads on the inner surface of the tube sleeve. Other methods of securing the fill/flush tube within the sleeve may be used. The fill/flush tube 90 includes a fill duct 92 through which replenishing solution, such as new cell solution or culture medium, flows. The tube 90 further includes one or more fill ports 96 which align with the filling ports 22 of the device 10c to enable passage of fluid therethrough. The fill/flush tube 90 further includes a flush duct 94 which, in one embodiment, is along the central axis of tube 90. The flush duct includes a flush port 98 which aligns with the insertion port 36 of the device 10c.

As shown in FIG. 12, the device 10c may further include center tube support fins 100 which stabilize the position of the fill/flush tube 80 when it is positioned at the ports of the device 10c. Other methods and devices for securing and stabilizing the fill/flush tube 90 may be used, and are known in the art. For instance, the refill/flush capabilities of the current invention also allow the introduction of therapeutic medicaments or other biologically active factors prior to the cell chambers without removal of the chambers contents.

In yet another embodiment of the present invention, shown in FIG. 13, the device 10f may include a filter basket 110 with a delivery sheath 112. The filter basket 110 is manufactured from a biocompatible micro-filter material generally commercially available. It may be sealed at the proximal end, and attached to an upper portion 114. Due to the problem of movement between the skull and the brain, discussed in further detail above, it is desirable that the upper section 114 be flexible to accommodate such movement. The upper portion 114 may be topped with a retaining screw 116, or other securing device.

As shown in FIG. 14, the filter basket 110 may be adapted to contain a membrane implant device 120 which enables constant, controlled flow of biologically active factors from the inner cell chamber, out into the desired treatment site. The implant device 120 may be a tethered cell chamber, as described above, or other device for containing biologically active factors. The illustrated device is replenishable by removing the retaining screw 116, or other plug or cap, and lifting the membrane implant device 120 or other cell chamber, out of the filter basket 110.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A refillable immunoisolatory therapeutic device for implantation through a human skull and into a human brain, comprising:

an outer flexible cell chamber adapted for containing viable cells which secrete at least one biologically active factor, the outer cell chamber having a first end connected to a cap, a second end for positioning within the brain, and at least one semipermeable surface across which the active factor secreted by the viable cells can be delivered at ambient pressure to the brain, the cell chamber being adapted for infusion with the viable cells and for protecting the cells from immunogens, an inner flushing duct with a proximal end and a distal end, the distal end open to the second end of the cell chamber, the cap adapted to engage an anchoring means, for anchoring the cell chamber and the inner flushing duct to the human skull, the cap having accessing means for accessing the cell chamber and the inner flushing duct to introduce, flush and renew the viable cells, the accessing means comprising an inner flushing duct port and an outer cell chamber port, the flushing duct port in fluid communication with the proximal end of the inner flushing duct, and the outer cell chamber port in fluid communication with the first end of the outer cell chamber, a mandrel to protect the cell chamber.

2. The device of claim 1 wherein the semipermeable surface is permeable to a biologically active factor selected from the group consisting of gamma aminobutyric acid, serotonin, acetylcholine, norepinephrine, endorphins, enkephalins, dopamine, and precursors, agonists, active analogs, and active fragments thereof.

3. The device of claim 2 wherein the biologically active factor is a dopamine precursor comprising L-dopa.

4. The device of claim 2 wherein the biologically active factor is a dopamine agonist comprising bromocriptine.

5. The device of claim 2 wherein the biologically active factor is dopamine.

6. The device of claim 1 wherein the cell chamber further comprises a hydrophobic matrix.

7. The device of claim 6 wherein the hydrophobic matrix comprises an ethylene-vinyl acetate copolymer.

8. The device of claim 1 wherein the cell chamber comprises a hydrophilic matrix.

9. The device of claim 8 wherein the hydrophilic matrix comprises a hydrogel.

10. The device of claim 1 wherein the cell chamber further comprises an impermeable outer coating covering a portion of the cell chamber.

11. The device of claim 10 wherein the impermeable outer coating comprises polyurethane.

12. The device of claim 10 wherein the impermeable outer coating comprises ethylene-vinyl acetate.

13. The device of claim 1 wherein the cell chamber further comprises an outer membrane including angiogenic factors.

14. A refillable immunoisolatory therapeutic device for implantation through a human skull and into a human brain, comprising:

a flexible cell chamber adapted for containing viable cells which secrete at least one biologically active factor, the cell chamber comprising a first end, a second end for positioning within the brain, a cell chamber exterior wall surface, and at least one semipermeable surface in the second end, across which the active factor secreted by the viable cells can be delivered to the brain, the cell chamber being adapted for infusion with the viable cells and for protecting the viable cells from immunogens;

the cell chamber constructed as a U-tube with the open free ends of the U-tube connected at the first end of the cell chamber to a cap, the cap adapted to engage a skull anchoring means, for anchoring the cell chamber to a human skull, the cap having accessing means comprising at least one port in fluid communication with at least one free end of the U-tube to introduce, flush and renew the viable cells, a substantially rigid mandrel adapted to engage at least a portion of the cell chamber exterior wall surface during implantation in the brain, wherein the mandrel engages at least a portion of the cell chamber exterior wall surface during implantation and the mandrel being removable through a insertion port in the cap after implantation.

15. The device of claim 14 wherein:

the mandrel includes a portion that expands to engage at least a portion of the exterior wall surface of the cell chamber during implantation of the device and selectively collapses to fit through the insertion port for removal.

16. The device of claim 14 further comprising an outer, substantially rigid shield, the shield comprising two legs, the legs being closeable around the cell chamber when the shield is fully inserted and the legs being outwardly flexible to form a gap around the cell chamber during insertion and removal of the shield, so that the shield slidably fits through the insertion port and over the mandrel.

17. The device of claim 16 wherein the shield has tab means for engaging the mandrel and the mandrel includes an aperture adapted to at least partially receive the tab means to enable interlocked removal of the mandrel and shield from the cell chamber.

18. The device of claim 14 wherein the semipermeable surface is permeable to a biologically active factor selected from the group consisting of gamma aminobutyric acid, serotonin, acetylcholine, norepinephrine, endorphins, enkephalins, dopamine, and precursors, agonists, active analogs, and active fragments thereof.

19. The device of claim 18 wherein the biologically active factor is a dopamine precursor comprising L-dopa.

20. The device of claim 18 wherein the biologically active factor is a dopamine agonist comprising bromocriptine.

21. The device of claim 18 wherein the biologically active factor is dopamine.

22. The device of claim 14 wherein the cell chamber further comprises a hydrophobic matrix.

23. The matrix of claim 22 wherein the cell chamber further comprises an ethylene-vinyl acetate copolymer.

24. The device of claim 14 wherein the cell chamber comprises a hydrophilic matrix.

25. The device of claim 24 wherein the hydrophilic matrix comprises a hydrogel.

26. The device of claim 14 wherein the cell chamber further comprises an impermeable outer coating covering a portion of the cell chamber.

27. The device of claim 26 wherein the impermeable outer coating comprises polyurethane.

28. The device of claim 26 wherein the impermeable outer coating comprises ethylene-vinyl acetate.

29. The device of claim 14 wherein the cell chamber further comprises an outer membrane including angiogenic factors.

* * * * *